United States Patent
Olivier-Bourbigou et al.

(10) Patent No.: US 7,906,663 B2
(45) Date of Patent: *Mar. 15, 2011

(54) PROCESS FOR CO-PRODUCING OLEFINS AND DIESTERS OR DIACIDS STARTING FROM UNSATURATED FATS

(75) Inventors: Hélène Olivier-Bourbigou, Saint Genis Laval (FR); Christophe Vallee, Fontaine (FR); Gérard Hillion, Herblay (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 1045 days.

This patent is subject to a terminal disclaimer.

(21) Appl. No.: 11/626,077

(22) Filed: Jan. 23, 2007

(65) Prior Publication Data

US 2007/0179307 A1 Aug. 2, 2007

(30) Foreign Application Priority Data

Jan. 24, 2006 (FR) ..................... 06 00646

(51) Int. Cl.
*C07C 51/00* (2006.01)
(52) U.S. Cl. ....................... 554/163; 560/190
(58) Field of Classification Search .................. 554/163; 560/190
See application file for complete search history.

(56) References Cited

U.S. PATENT DOCUMENTS 6,756,500 B1 6/2004 Gurtler et al.
7,678,932 B2 * 3/2010 Thurier et al. ................ 554/124

FOREIGN PATENT DOCUMENTS

EP 1 698 686 A 9/2006

OTHER PUBLICATIONS

Olivier-Bourbigou H et al., Ionic Liquids: Perspectives for Organic and Catalytic Reactions, Journal of Molecular Catalysis, 2002, pp. 419-437.
Warwell S. et al., Polymers and Surfactants on the Basis of Renewable Resources, Chemosphere, 2001, pp. 39-48, vol. 43.

* cited by examiner

*Primary Examiner* — Deborah D Carr
(74) *Attorney, Agent, or Firm* — Millen, White, Zelano & Branigan, P.C.

(57) ABSTRACT

In order to produce both an olefinic fraction and a composition of diacids or diesters of fats, a process is carried out which comprises, in succession:
a) metathesis of an unsaturated fat with ethylene in the presence of at least one non-aqueous ionic liquid;
b) separating and recycling the ionic liquid used in the first step;
c) separating, by distillation, the olefinic fraction (fraction A) from the unsaturated fat mono-ester or mono-basic acid fraction (fraction B) formed in step a);
d) homometathesis of the mono-unsaturated fat ester or acid cut (fraction B) which allows the co-production of unsaturated fat diesters or diacids (fraction C) and ethylene which is recycled to the first methathesis step of the process; and
e) optionally, recycling the ionic liquid containing the catalyst used in step d).

Of particular application to an oleic sunflower oil, an oleic rapeseed oil or to a mixture of mono-alcohol esters of said oils, whereupon the process can produce both an olefinic fraction (mainly composed of 1-decene) and a composition of diesters or diacids wherein, in general, over half of the chains is constituted by unsaturated $C_{18}$ chains (mainly composed of octadecene-9 1,18-iacid or diester) and to recycle the ethylene employed.

14 Claims, 2 Drawing Sheets

PROCESS FOR CO-PRODUCING OLEFINS AND DIESTERS OR DIACIDS STARTING FROM UNSATURATED FATS

FIELD OF THE INVENTION

The invention relates to a process for co-producing olefins and unsaturated diesters or diacids from unsaturated fats.

PRIOR ART

Alpha olefins, more particularly 1-decene, are desirable synthesis intermediates in petrochemistry and are usually entirely manufactured from fossil starting materials such as ethylene. 1-decene is especially important in the manufacture of poly-alpha-olefins (PAO) which are synthesized lubricants and are used in the preparation of alcohols and in many other industrial chemistry manufacturing processes. The manufacture of such olefins from a starting material which is essentially animal or vegetable in origin, and thus renewable, is potentially of huge interest.

Long chain diesters or diacids, and more particularly 9-octadecene-1,18-dioic acid, a desirable intermediate in the manufacture of certain polymers, are generally obtained by fermenting paraffins derived from petroleum. Their manufacture from a starting material which is essentially animal or vegetable in origin and thus renewable is also of huge potential interest.

Said two compounds may be obtained independently from starting materials of vegetable or animal origin, for example from unsaturated fatty acids or esters which are mainly present in vegetable oils, by methathesis reactions.

The Applicant's French patent application FR-2 878 246 describes a reaction for methathesis of an unsaturated fat with ethylene, in the presence of at least one non-aqueous ionic liquid, which can produce both an olefinic fraction and a composition of mono-alcohol or polyol esters. More particularly, when applied to an oleic sunflower seed oil, to an oleic rapeseed oil or to a mixture of mono-alcohol esters of said oils, the process can produce both an olefinic fraction and a composition of mono-alcohol or glycerol esters more than half of the chains of which is generally constituted by unsaturated $C_{10}$ chains.

The Applicant's French patent application FR 06/00645 filed on 24 Jan. 2006 describes a process in which an unsaturated fat is reacted, by a homometathesis reaction, in the presence of at least one non-aqueous ionic liquid, to produce both a long chain olefinic fraction the double bond of which is in an internal position and a composition of mono-alcohol diesters or diacids. More particularly, when applied to a mixture of an ester of an oleic sunflower seed oil or an oleic rapeseed oil, the process can produce both an olefinic fraction and a composition of mono-alcohol or diacid diesters wherein more than half of the chains is generally constituted by unsaturated $C_{18}$ chains.

Aim of the Invention

The present invention proposes a process for co-producing olefins and unsaturated diesters or diacids including:
a) a step for metathesis of at least one unsaturated fat which is rich in unsaturated esters or fatty acids with ethylene in the presence of at least one non-aqueous ionic liquid and at least one catalyst;
b) a step for separating and recycling the ionic liquid containing the catalyst used in the step a);
c) a step for separating the olefins and the unsaturated esters or acids produced in step a);
d) a step for homometathesis of the mono-unsaturated esters or acids produced in step a) and separated in step c), carried out in the liquid phase in the presence of at least one catalyst; and
e) optionally, a step for separating and recycling the ionic liquid containing the catalyst when used in step d).

This succession of steps can simultaneously produce mainly olefins the double bond of which is in the terminal position (alpha olefins) and mainly unsaturated long chain diesters or diacids. One of the advantages of this process is that the ethylene co-produced in step d) of the process can be re-used by recycling it to the inlet to the first methathesis step.

The invention also concerns a facility used to carry out the process of the invention.

DETAILED DESCRIPTION OF THE INVENTION

Figure 1:
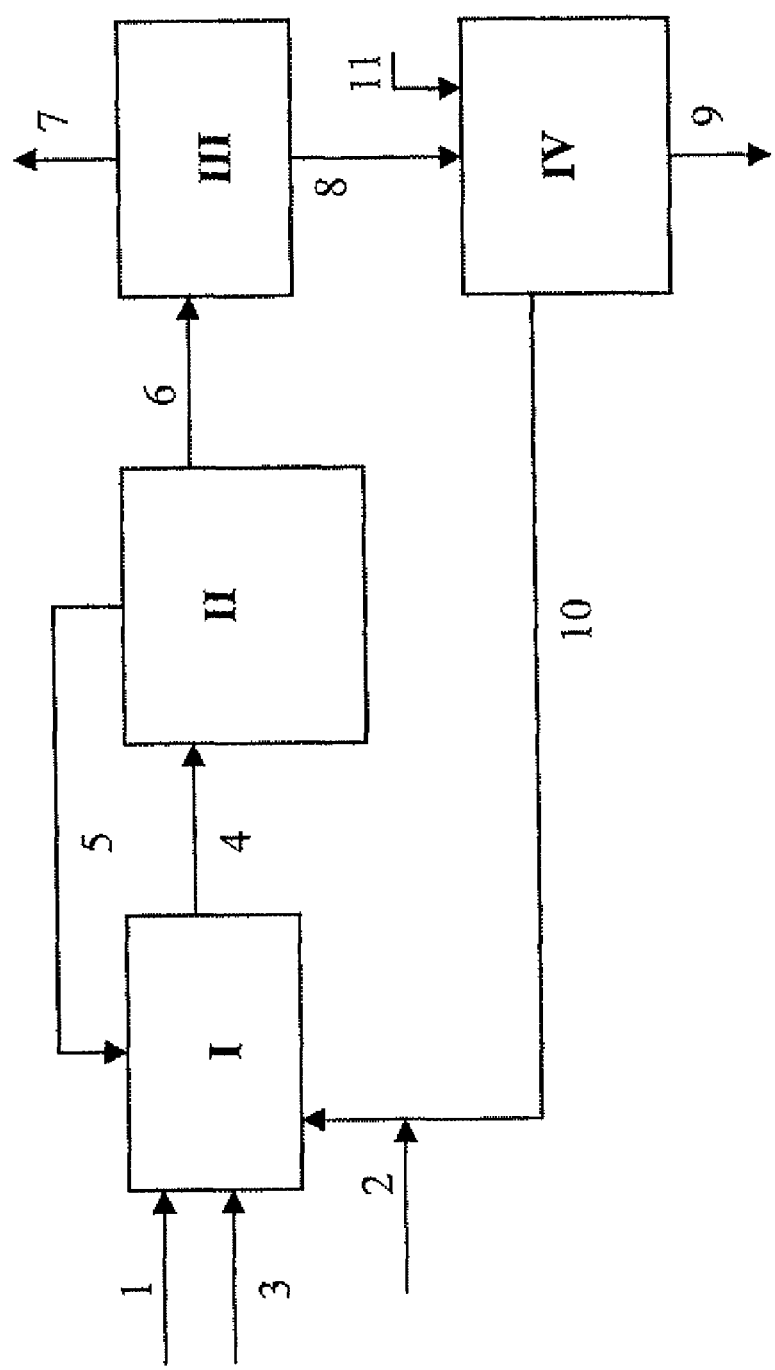
FIG. 1 shows a flow scheme of a facility for carrying out the process of the invention.

The feeds treated in the process of the invention are unsaturated fats comprising at least one carboxylic monoacid containing 12 to 22 carbon atoms and comprising at least one ethylenically unsaturated bond and/or a monoester formed between said monoacid and at least one mono-hydroxylated saturated aliphatic compound (mono-alcohol), the mono-alcohol being a mono-alcohol containing 1 to 8 carbon atoms, for example.

More particularly, the process of the invention is of particular application to oleic acid, a fatty acid the chain of which carries a single unsaturated bond, or its derivative esters. In this case, the process produces only two products, 1-decene and the 1,18-diacid of 9-octadecene or the corresponding diester.

However, no fat of vegetable or animal origin exists in nature the fatty chains of which are exclusively constituted by oleic chains. Thus, obtaining a pure oleic acid ester necessitates the use of a separation and purification operation which usually employs distillation under difficult conditions, rendering it expensive.

The nature of the products obtained and their quantity will thus depend on the composition of the fatty acids (nature and abundance) of the starting fat which is used.

Producing products which are rich in 1-decene involves the use or a starting material which is rich in oleic acid esters.

Said oils are preferably used in the form of a mixture of esters of mono-alcohols such as methanol, ethanol, propanol or, more generally, any mono-alcohol containing 1 to 8 carbon atoms.

Saturated fatty acid esters present in oleic sunflower seed oil or oleic rapeseed oil or in mono-alcohol esters of said oils are not reactive in methathesis reactions and are recovered at the end of the operation.

The vegetable oil under consideration (or the mono-alcohol ester of that oil) is preferably selected from oleic sunflower seed oil or oleic rapeseed oil (or mono-alcohol esters of said oils). These particular oils and mono-alcohol esters derived from these oils are characterized by their fatty acid composition, in particular by the nature and the proportion of their unsaturated fatty acids. In these oils or mono-alcohol esters of these oils, in general at least 80% of the fatty acid chains are constituted by oleic chains ($C_{18}$); the linoleic fatty chain content does not exceed 12% and the linolenic fatty chain content does not exceed 0.3%. No other olefinic chain is present in said oils or in the mono-alcohol esters or said oils in an amount of more than 0.3%, while the amount of the saturated chains, for example palmitic or stearic, is in the range 5% to 15%.

As an example, consider a methyl ester of an oleic sunflower seed oil with the following composition:

| | |
|---|---|
| methyl oleate: | about 83% by weight; |
| methyl linoleate: | about 10% by weight; |
| methyl palmitate: | about 3% by weight; |
| methyl stearate: | about 4% by weight. |

The particular conditions of the various steps of the process of the invention will now be considered, carried out using a fat containing at least one ethylenically unsaturated bond, and aimed at simultaneously producing an olefinic fraction mainly composed of alpha olefins and an unsaturated long chain diester or diacid.

The main aim of the first step a) is to transform the unsaturated ester or fatty acid derived from a vegetable oil, in particular a methyl ester of an oleic sunflower seed oil the composition of which was detailed above:

firstly, into an olefinic fraction mainly of 1-decene (fraction A);

and then into a mixture of esters wherein over half of the chains is constituted by unsaturated $C_{10}$ chains (fraction B). Said composition does not correspond to any known fat. Such a mixture of esters is characterized in that its concentration of unsaturated $C_{10}$ chains is very high. It is also characterized by the position of the unsaturated bond located between the carbon atom in position 9 and that in position 10 on the carbonaceous chain. This position of the unsaturated bond is different from that observed in natural products.

This first step involves methathesis of the unsaturated fats, of the type described above, with an excess of ethylene. It is carried out in the presence of at least one catalyst and in the presence of at least one non-aqueous ionic liquid as disclosed in the Applicant's French patent application FR-2 878 246 cited above.

In this step, the catalyst (for example based on a ruthenium complex) is advantageously used in the non-aqueous ionic liquid, with which the products formed are very slightly miscible. The catalyst is immobilized and stabilized in the ionic liquid. This liquid, containing the catalyst, may be recycled and re-used.

The catalysts used in this first step of the process comprising methathesis of the unsaturated fats with excess ethylene may consist of any known methathesis catalyst, in particular catalysts comprising at least one ruthenium compound.

The non-aqueous ionic solvent is selected from the group formed by liquid salts which have general formula $Q^+A^-$, in which $Q^+$ represents a quaternary ammonium, a quaternary phosphonium, a quaternary guanidinium or a quaternary sulphonium and $A^-$ represents any anion which can form a liquid salt at low temperatures, i.e. below 90° C. and advantageously at most 85° C., preferably below 50° C.

According to the process of the invention, the methathesis reaction of step a) of the process is carried out with ethylene used in excess. The reaction may be carried out in the absence or in the presence of an organic co solvent. In the case in which a solvent or a mixture of solvents is used, its role may be to improve dissolution of the reagents and the catalyst in the ionic liquid. It may also act to optimize extraction of products into a second phase. Examples of solvents which may be envisaged are chloroalkanes such as dichloromethane, chloroform or dichloro-or trichloro-methane, aromatic solvents such as toluene, xylenes or chlorobenzene, or aliphatic solvents such as heptane or cyclohexane.

Methathesis of an unsaturated fat (monoacid or mono ester) derived, for example, from oleic sunflower seed oil or oleic rapeseed oil with ethylene, used in excess, may be carried out in a closed (batch) system, in a semi-open or in a continuous system with one or more reaction stages.

Vigorous agitation must ensure good contact between the reagents (gas and liquid) and the catalytic mixture. The reaction temperature may be from 0° C. to +150° C., preferably 20° C. to 120° C.

The operation may be carried out above or below the melting point of the medium, the dispersed solid stage not being a limitation to the proper course of the reaction.

The pressure may, for example, be from atmospheric pressure to 50 MPa.

The ethylene may be used pure or mixed or diluted with a paraffin (inert).

The second step b) of the process of the invention consists of separating the ionic liquid phase containing the catalyst from the phase containing the products of the methathesis reaction carried out in the first step. In this second step, the reaction products from the first methathesis step may be separated from the ionic liquid containing the catalyst either by distillation if the ionic liquid is non-volatile, or by decanting if the solubility of the olefins formed in the ionic liquid is low.

The third step c) of the process of the invention consists of separating the products formed during the first methathesis step of the process of the invention. The purely olefinic fraction (fraction A constituted by mono-and di-olefins, mainly composed of 1-decene) can easily be separated from the fraction B constituted by a mixture of the esters (or acids) which are present (mainly methyl decenoate) by an evaporation step, depending on the boiling point difference of the two fractions.

In the process of the present invention, the mixture of olefins isolated above (fraction A) may undergo distillation to separate the di-olefins and the mono-olefins, as well as any excess ethylene. The excess ethylene may be recycled to step a) of the same process or it may be used during a new methathesis reaction, while each of the other mono-(or di-) olefins may be upgraded and used separately.

After evaporating off the purely olefinic fraction A, the residual reaction medium (fraction B), as a consequence, contains a mixture of esters, i.e. an ester of 9-decenoic acid in the mono-alcohol ester from, or in the form of an acid and also possibly acids or esters of saturated acids present in the starting material, i.e. palmitic and stearic acids in the form of mono-alcohol esters or in the acid form, depending on the starting material used. Said saturated structures are not involved in the methathesis reaction.

The fourth step d) of the process of the invention consists of the fraction B constituted by unsaturated esters or acids undergoing a homometathesis reaction.

The catalysts used in this forth step of the process to carry out homometathesis of the unsaturated esters or acids may consist of any known methathesis catalyst, in particular catalysts comprising at least one ruthenium compound.

Said homometathesis reaction is carried out in the liquid phase. The catalyst may be used in a non-aqueous ionic liquid as described in step a) of the process.

It is also possible to envisage carrying out the reaction in the absence of solvent or in the presence of an organic solvent. Examples of solvents which may be envisaged for the invention which may be cited are chloroalkanes such as dichloromethane, chloroform or dichloro-or trichloro-ethane, aromatic solvents such as toluene, xylenes, or chlorobenzene, or aliphatics such as heptane or cyclohexane.

The reaction temperature may be from 0° C. to +150° C., preferably 20° C. to 120° C.

The methathesis reaction in this fourth step of the process may be carried out in a semi-open batch system or in a continuous system with one or more reaction stages.

The gaseous ethylene which is co-produced in this step is separated and transferred to step a) of the process of the invention.

Figure 2:
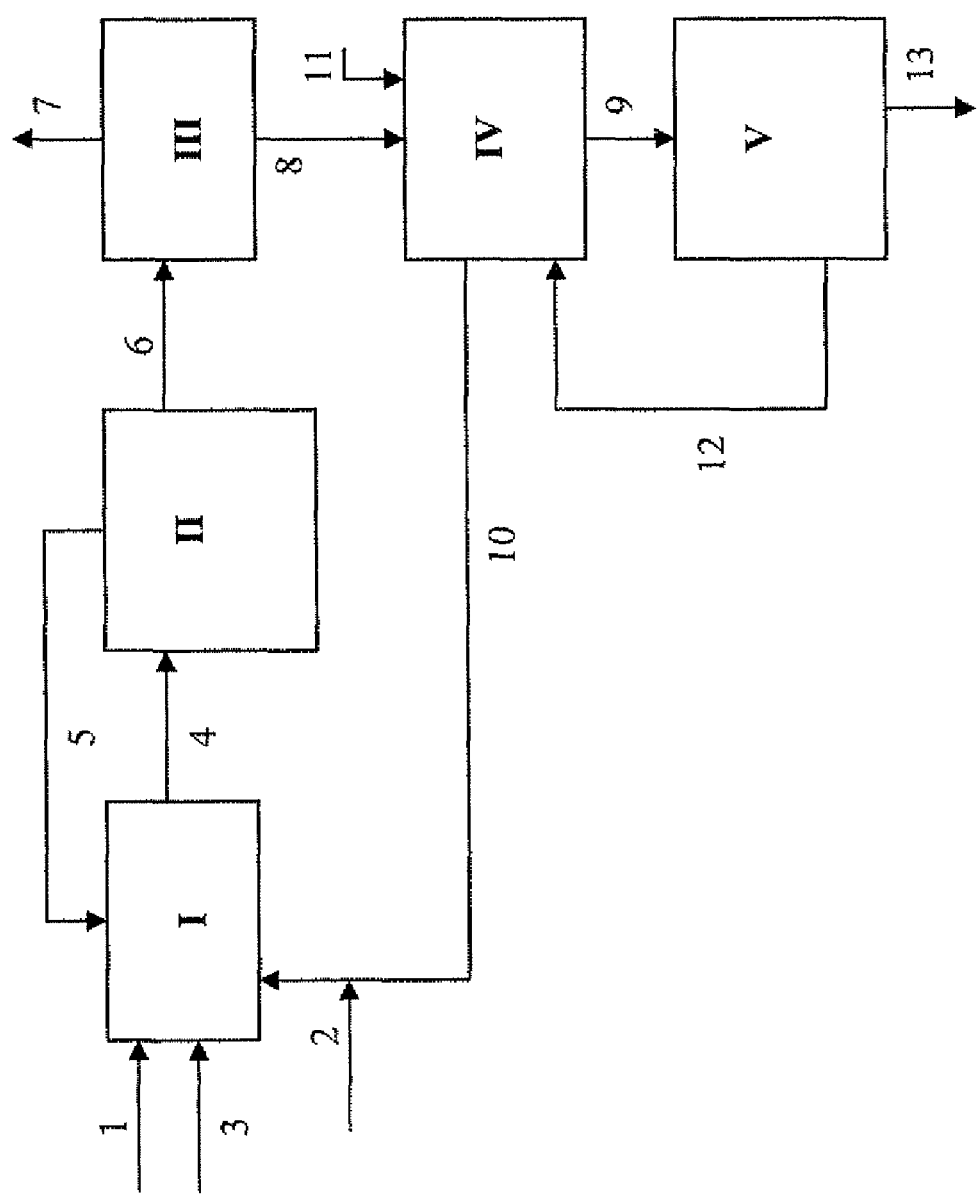
FIG. 2 shows a flow scheme of a facility for carrying out the process of the invention comprising a step for recycling the ionic liquid used in the homometathesis reaction.

In the case in which the homometathesis reaction carried out in step d) uses an ionic liquid as the solvent for the catalyst, the process of the invention may comprise a fifth step e) which consists of separating the ionic liquid containing the catalyst from the reaction products and recycling the ionic liquid to the inlet to methathesis step d) in the same manner as after step b) (shown in FIG. 2).

The invention also concerns a facility (shown in FIGS. 1 and 2) used to carry out the process described above.

It is constituted by different zones in which the various steps of the process of the invention take place in succession:
- a zone I for methathesis of unsaturated fats with an excess of ethylene, said zone I comprising at least one means 1 for introducing unsaturated fat, at least one means 2 for introducing ethylene, and at least one means 3 for introducing catalyst. The effluent from said zone I is removed via at least one means 4;
- a zone II in which the ionic liquid is recycled. In this zone, the ionic liquid containing the catalyst is separated from the effluent from zone I, said zone comprising at least one means 4 for introducing effluent from zone I, at least one means 5 for recycling the ionic liquid containing the catalyst to the inlet to zone I, at least one means 6 for removing the organic phase containing the olefinic fraction and the unsaturated ester or fatty acid fraction;
- a zone III for separating organic effluent from zone II, comprising at least one means 6 for introducing effluent from zone II, at least one means 7 for removing olefinic fraction A, and at least one means 8 for removing a fraction B constituted by unsaturated esters or fatty acids;
- a zone IV in which the homometathesis reaction takes place, comprising at least one means 8 for introducing effluent to be converted derived from zone III, at least one means 9 for removing effluent principally containing the unsaturated long chain diester or diacid formed, at least one means 10 for separating the gaseous ethylene co-produced by the homometathesis reaction, the means 10 for separating ethylene in said zone IV being connected to the means 2 for introducing ethylene into zone I, and at least one means 11 for introducing catalyst.

In the case in which the methathesis reaction of zone IV is carried out in the presence of an ionic liquid, the process of the invention may optionally include:
- a zone V for separating the ionic liquid containing the catalyst from the effluent formed, comprising at least one means 12 for separating the ionic liquid and recycling it to the inlet to zone IV, and at least one means 13 for separating the effluent formed in said zone (shown in FIG. 2).

The following examples illustrate the invention without limiting its scope.

EXAMPLE 1

Metathesis by Ethenolysis of Methyl Oleate Catalyzed by a Type 3 Complex (FIG. 1) in an Ionic Liquid 1 ml of 3-butyl-1,2-dimethylimidazolium bis-triflylamide with formula $[BMMI]^+[N(CF_3SO_2)_2]^-$ pre-dried overnight at 80° C., 148 mg of methyl oleate (source: Fluka, with a purity higher than 98%) and 15 mg of the complex with formula $Cl_2Ru(=CH\text{-}o\text{-}O\text{-}iPrC_6H_4)PCy_3$ (synthesized by reacting the 1$^{st}$ generation Grubbs complex with formula $Cl_2Ru(=CHC_6H_5)(PCy_3)_2$ with 1-isopropoxy-2-vinylbenzene in the presence of CuCl), this corresponding to 5% molar of catalyst with respect to methyl oleate, were introduced, in an inert atmosphere of argon, into an autoclave reactor provided with an agitation system and a pressure sensor. The autoclave was then placed under vacuum and pressurized to obtain a pressure of 10 bars (1 MPa) of ethylene (origin: Alphagas, quality N25). The temperature was kept constant at 20° C.

The medium was stirred at ambient temperature for 2 hours, then the excess ethylene was slowly purged by returning to atmosphere pressure at a temperature not exceeding 20° C. and the autoclave was again placed under an atmosphere of argon. The products were separated from the ionic liquid by adding 2 to 3 ml of heptane distilled over $CaH_2$ and degassed. An aliquot (100 µl) of the extracted solution was passed through a short silica column (2 cm) eluted with diethyl ether. It was analyzed by gas phase chromatography (ZB-1 column, 100% dimethylpolysiloxane, 30 metres, helium vector gas 2 ml/min, temperature programming: 60° C. then 5° C./min to 220° C.) coupled to a mass spectrometer.

The methyl oleate conversion was 95%. It was calculated using decane as an internal reference. The reaction products were composed of 1-decene (fraction A) and methyl decenoate (fraction B).

The presence of 1-decene isomers was not detected. Homo-metathesis products were present in trace amounts and could not be quantified.

EXAMPLE 2

Recycling Ionic Liquid Containing Catalyst

After the first cycle carried out in accordance with Example 1, the autoclave containing the ionic liquid and the catalyst was placed under vacuum to eliminate traces of heptane. In an argon atmosphere, 148 mg of methyl oleate was added then the reactor was pressurized to obtain a pressure of 10 bars (1 MPa) of ethylene. The temperature was kept at 20° C.

The same procedure as that described in Example 1 was carried out to analyze the products formed.

3 successive cycles were carried out without adding catalyst or ionic liquid.

The methyl oleate conversion and the composition of the products formed were determined for each cycle (Table 1 below).

TABLE 1

| | Methyl oleate conversion (wt %) | Products formed |
|---|---|---|
| 1$^{st}$ cycle (Example 1) | 95 | 1-decene + methyl decanoate |
| 2$^{nd}$ cycle | 95 | 1-decene + methyl decanoate |
| 3$^{rd}$ cycle | 85 | 1-decene + methyl decanoate |

EXAMPLE 3

Biphasic Homometathesis of Methyl Decenoate in Ionic Liquid

To a glass reaction flask were added (50 mg, 0.062 mmol, 0.01 eq.) (1,3-Bis-(2,4,6-trimethylphenyl)-2-imidazolidinylidene) dichloro(benzylidene)(tricyclohexylphosphine) ruthenium, 1.5 mL (6.62 mmol, 1 eq.) methyl decenoate obtained after the separation of the two fractions produced in the Example 1, 1 mL 1-butyl-1-methylpyrrolidinium bis(trifluoromethanesulfonyl)amide (BMPyrr)(NTf2), 2 mL heptane and 0.1 mL of dodecane as internal standard. The mixture was biphasic. It was stirred and heated at room temperature. After 2 hours reaction time, a small aliquot of the liquid upper phase was removed for GC analysis. GC analysis indicated that the metathesis reaction had proceeded cleanly, yielding dimethyloctadecene-1,18-dioate products. Conversion of methyl 9-decenoate to these products was 70 wt %.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 06/00.646, filed Jan. 24, 2006, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for producing both an olefinic fraction and a composition of diesters or diacids from unsaturated fats, characterized in that it comprises a succession of steps including:
   a) a step for bringing into contact, under methathesis conditions, at least one unsaturated fat comprising at least one carboxylic monoacid containing 12 to 22 carbon atoms and comprising at least one ethylenically unsaturated bond or a monoester of said monoacid, with excess ethylene, in the presence of a catalyst and in the presence of at least one non-aqueous ionic liquid, jointly producing an olefinic fraction and a fraction of monoesters or monoacids of unsaturated fats;
   b) a step for separating and recycling ionic liquid containing the catalyst used in step a);
   c) a step for separating the olefinic fraction (fraction A) and the unsaturated fat monoester or monoacid fraction (fraction B) produced in step a);
   d) a step for homometathesis of fraction B of unsaturated fat monoesters or monoacids separated in step c), said homometathesis being carried out in the liquid phase in the presence of at least one catalyst.

2. A process according to claim 1, characterized in that in step a) it employs a feed constituted by an unsaturated fat comprising at least one ester formed between at least one carboxylic monoacid comprising at least one ethylenically unsaturated bond and containing 12 to 22 carbon atoms and at least one monohydroxylated aliphatic compound (mono-alcohol) containing 1 to 8 carbon atoms.

3. A process according to claim 1, characterized in that in step a) it employs an unsaturated fat selected from mixtures of mono-alcohol esters of oleic sunflower seed oils and oleic rapeseed oils to produce both an olefinic fraction A and a composition of mono-alcohol esters at least a portion of the chains of which is constituted by unsaturated $C_{10}$ chains (fraction B).

4. A process according to claim 3, characterized in that the feed introduced in step a) is a methyl ester of an oleic sunflower seed oil with the following composition:
   methyl oleate: about 83% by weight;
   methyl linoleate: about 10% by weight;
   methyl palmitate: about 3% by weight;
   methyl stearate: about 4% by weight.

5. A process according to claim 4, characterized in that the fraction A obtained is mainly 1-decene and fraction B is mainly methyl 9-decenoate.

6. A process according to claim 1, characterized in that the non-aqueous ionic liquid is selected from the group formed by liquid salts with general formula $Q^+A^-$ in which $Q^+$ represents a quaternary phosphonium, a quaternary ammonium, a quaternary guanidinium or a quaternary sulphonium and $A^-$ represents any anion which is capable of forming a liquid salt below 90° C.

7. A process according to claim 1, characterized in that at least one ruthenium compound is used as the catalyst in steps a) and d).

8. A process according to claim 1, characterized in that step b) is a step for separating the ionic liquid phase containing the catalyst and the reaction products from step a) either by distillation or by decanting.

9. A process according to claim 1, characterized in that it comprises a step for separating fractions A and B by evaporation during step c).

10. A process according to claim 9, characterized in that it further comprises a step in which the mono olefins and the di-olefins of fraction A are separated by distillation.

11. A process according to claim 3, characterized in that the feed introduced in step d) is an ester of 9-decenoic acid in the mono-alcohol ester form.

12. A process according to claim 1, characterized in that it comprises a step for extracting the ethylene co-produced during step d) to re-use the ethylene in step a).

13. A process according to claim 1, characterized in that homometathesis of step d) is carried out in the presence of a non-aqueous ionic liquid containing the catalyst.

14. A process according to claim 13, characterized in that the process further comprises a step for separating and recycling the ionic liquid used in step d) containing the catalyst.

* * * * *

UNITED STATES PATENT AND TRADEMARK OFFICE
CERTIFICATE OF CORRECTION

PATENT NO. : 7,906,663 B2  
APPLICATION NO. : 11/626077  
DATED : March 15, 2011  
INVENTOR(S) : Hélène Olivier-Bourbigou et al.

Page 1 of 1

It is certified that error appears in the above-identified patent and that said Letters Patent is hereby corrected as shown below:

Title Page, Item (57), Abstract, lines 26 and 27 reads "octadecene-9 1,18-iacid or diester) and to recycle the ethylene employed." should read --octadecene-9 1,18-diacid or diester) and to recycle the ethylene employed.--

Signed and Sealed this  
Twelfth Day of July, 2011

David J. Kappos  
*Director of the United States Patent and Trademark Office*